(12) United States Patent
Frigg et al.

(10) Patent No.: US 10,932,830 B2
(45) Date of Patent: Mar. 2, 2021

(54) DEVICE FOR BONE FIXATION

(71) Applicant: 41 medical AG, Bettlach (CH)

(72) Inventors: Robert Frigg, Bettlach (CH); Patrick Burki, Bern (CH); Daniel Fluri, Bettlach (CH)

(73) Assignee: 41medical AG, Bettlach (CH)

( * ) Notice: Subject to any disclaimer, the term of this patent is extended or adjusted under 35 U.S.C. 154(b) by 105 days.

(21) Appl. No.: 16/072,664

(22) PCT Filed: Feb. 19, 2016

(86) PCT No.: PCT/CH2016/000032
§ 371 (c)(1),
(2) Date: Jul. 25, 2018

(87) PCT Pub. No.: WO2017/139903
PCT Pub. Date: Aug. 24, 2017

(65) Prior Publication Data
US 2019/0029741 A1 Jan. 31, 2019

(51) Int. Cl.
*A61B 17/80* (2006.01)
*A61B 17/84* (2006.01)
*A61B 17/86* (2006.01)

(52) U.S. Cl.
CPC ...... *A61B 17/8047* (2013.01); *A61B 17/8605* (2013.01); *A61B 17/866* (2013.01)

(58) Field of Classification Search
CPC .............. A61B 17/866; A61B 17/8057; A61B 17/8047; A61B 17/8605; A61B 17/8052; A61B 17/86

USPC .................................... 606/70–71, 280–321
See application file for complete search history.

(56) References Cited

U.S. PATENT DOCUMENTS

| | | | | |
|---|---|---|---|---|
| 6,206,881 B1 * | 3/2001 | Frigg | ................. | A61B 17/8052 606/291 |
| 8,784,458 B1 | 7/2014 | White et al. | | |
| 2004/0254579 A1 * | 12/2004 | Buhren | .............. | A61B 17/8033 606/71 |
| 2006/0058797 A1 * | 3/2006 | Mathieu | ............. | A61B 17/8047 606/54 |
| 2006/0122602 A1 * | 6/2006 | Konieczynski | .... | A61B 17/7059 606/281 |
| 2007/0265629 A1 | 11/2007 | Martin et al. | | |
| 2008/0234677 A1 * | 9/2008 | Dahners | ............. | A61B 17/8047 606/60 |

(Continued)

FOREIGN PATENT DOCUMENTS

EP 2801330 A1 11/2014
WO 2004049962 A1 6/2004

*Primary Examiner* — Jessica Weiss
(74) *Attorney, Agent, or Firm* — Rankin, Hill & Clark LLP

(57) ABSTRACT

A device for bone fixation comprising: a bone plate (1) which has a plate hole (2) suitable for receiving a bone screw (20), the plate hole (2) having an inner wall (4) made of a material which has a hardness $H_p$; and a hollow cylinder- or hollow cone-shaped insert which is mounted in the plate hole (2), at least partially abuts the inner wall (4) and is suitable for accommodating the head (21) of a bone screw (20), the insert (10) being arranged in the plate hole (2) such that it is secured against rotation and consisting of a material that has a hardness $H_E < H_p$.

13 Claims, 3 Drawing Sheets

(56) References Cited

U.S. PATENT DOCUMENTS

| | | | |
|---|---|---|---|
| 2010/0305569 A1* | 12/2010 | Leuenberger | A61B 17/8023 606/70 |
| 2011/0224737 A1* | 9/2011 | Lewis | A61B 17/1728 606/290 |
| 2013/0190829 A1* | 7/2013 | Batsch | A61B 17/8014 606/291 |
| 2014/0271029 A1* | 9/2014 | Arnett | F16B 39/28 411/259 |
| 2015/0150610 A1 | 6/2015 | Impellizzeri | |
| 2019/0269444 A1* | 9/2019 | Schneider | A61B 17/8033 606/71 |

* cited by examiner

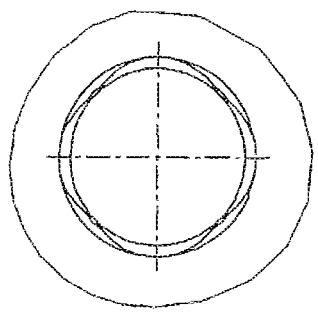
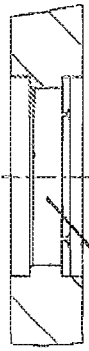
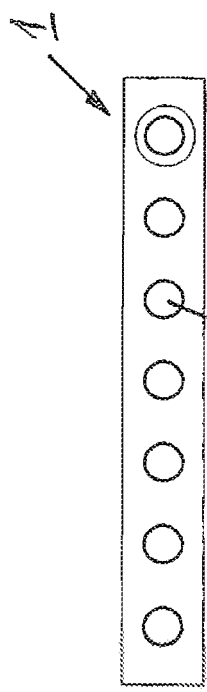
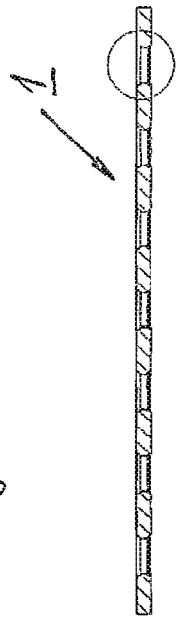
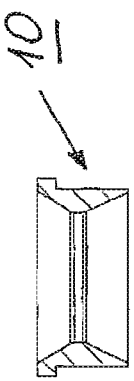
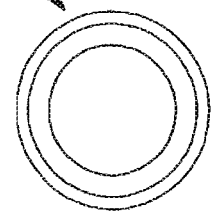
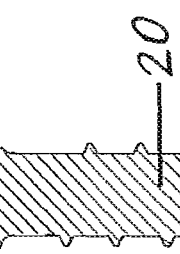

DEVICE FOR BONE FIXATION

The invention relates to a device for bone fixation.

The invention is based on the problem of creating a device for bone fixation which permits a secure connection between the construct bone screw/insert/bone plate and therefore guarantees a secure anchoring of the construct as a whole on the bone, wherein the risk of the rotating of the insert in the plate is minimized during the locking procedure and of the resulting tearing out of the previously formed thread in the bone.

The invention solves the problem posed by a device for bone fixation which has the features claimed herein.

The advantages achieved by the invention are substantially the fact that due to the special pairing of material during the introducing of a bone screw with a thread chat head into the plate hole provided with the insert, the knife-shaped flanks of the screw head thread displace the material of the insert—which is relatively soft in comparison to the bone plate material—so that a fixed compound is achieved between the screw head—the insert—and the bone plate.

Furthermore, a cold welding between the screw and the plate is prevented by the different materials, which is especially relevant during a revision of the plate.

Other advantageous embodiments of the invention can be commented on as follows:

In a special embodiment the bone plate consists of a material with the same hardness as the material of the inner wall of the plate hole.

In another embodiment the Vickers hardness of the material of the insert is in the range of 20 to 90% of the Vickers hardness of the material of the bone plate.

In another embodiment the Vickers hardness of the material of the insert is in the range of 120 to 200 HV.

In another embodiment the Vickers hardness of the material of the insert is in the range of 201 to 600 HV.

In another embodiment the bone plate and the insert consist of a metal or of a metal alloy.

In another embodiment the bone plate consists of a steel alloy.

In yet another embodiment the bone plate consists of pure titanium or of a titanium alloy.

In yet another embodiment the bone plate consists of a cobalt-chromium-molybdenum alloy.

In another embodiment the insert consists of pure titanium, preferably of titanium grade 2.

In another embodiment the plate hole is provided with means which allows the receiving of the insert in the plate bore in a manner security against rotation. This embodiment can be realized, e.g., by one or more projections from the inner wall of the plate hole and notches, slits corresponding to the projections or by the use of through bores. The rotation-proof receiving of the insert in the plate hole can also be realized by the projections on the outer wall of the insert and by notches in the inner wall of the plate hole which fit it.

In another embodiment the plate hole has an out of round or cylindrically interrupted shape. The plate hole preferably has the shape of a circle with at least one lacking circular segment or the shape of at least two partially overlapping circles.

In another embodiment the plate hole has an elliptical shape.

In another embodiment the plate hole has a central axis, wherein the insert is arranged concentrically to the central axis. The advantage of this embodiment is that a concentric hole-ring construct has an elevated angular stability. A ring which can incline in the hole can not be compressed as well, i.e., the pressing between ring and plate is lowered compared to a concentric construct.

In another embodiment the rotation-proof receiving of the insert in the plate hole is positively realized. This secures the insert against shifting, pivoting and rotating inside the plate hole.

In another embodiment the rotation-proof receiving the insert in the plate hole is realized by a stop in the plate hole.

In another embodiment the insert has a continuous slot. The slot makes possible the mounting of the insert in the plate hole by elastic deformation of the interrupted geometry.

In another embodiment the insert has a cross section in the shape of a circle with at least one lacking circular segment.

In another embodiment the insert has a cross section with substantially the shape of a polygon, preferably of a triangle. In an additional embodiment the corners of the polygon are rounded.

In another embodiment the insert is firmly connected to the bone plate.

In a special embodiment the bone plate (without insert) is constructed in one part.

In another embodiment the plate hole is constructed cylindrically.

In yet another embodiment the plate hole is conically constructed. This embodiment makes possible a self-locking of the insert and of the plate hole.

In another embodiment the semi-conical angle $\alpha$ of the plate hole is in the range of $40°>\alpha>0°$, preferably in the range of $20°>\alpha>0°$.

In another embodiment the insert is arranged in a self-locking manner in the plate hole.

In another embodiment the insert is secured against axial shifting in the plate hole. This can take place, for example, by everting material or by shouldering in the plate hole.

In another embodiment the insert has a shape which is at least partially congruent to the plate hole.

In another embodiment the outside diameter of the insert is greater than the inside diameter of the plate hole.

In another embodiment the insert is not held by a press-fit in the plate hole. This avoids that the two parts can disconnect.

In a special embodiment the device comprises a bone screw which comprises a head with an outside thread.

In another embodiment the outside thread of the screw head is multiply threaded.

In another embodiment the thread pitch of the head thread is in the range between 1 mm and 4 mm.

In another embodiment the outer thread of the screw head is a single thread.

In another embodiment the thread pitch of the head thread is in the range between 0.2 mm and 1 mm.

In another embodiment the outer thread of the screw head has a thread depth of at least 0.1 mm. The advantage of this embodiment is that the thread flanks of the outer thread can cut into the insert by cold deformation without chips with it. As a consequence, the insert-plate construct receives a better angular stability, i.e., it is capable of receiving a higher torque in the sense of angular stability.

In another embodiment the head of the bone screw tapers at least partially in the direction of the screw tip.

In another embodiment the bone screw head consists of a material whose hardness is greater than the hardness of the insert material. As a result, the locking of the screw head by the deformation of the softer insert by the harder material of the screw head is achieved.

In another embodiment the bone screw head consists of a steel alloy, e.g., implant steel 1.4441.

In another embodiment the bone screw head consists of titanium.

In another embodiment the Vickers hardness of the material of the bone screw (20) is in the range of 110 to 500% of the Vickers hardness of the insert material.

In another embodiment the Vickers hardness of the material of the bone screw and the Vickers hardness of the material of the bone plate are identical. The bone screw and the bone plate preferably consist of the same material.

In another embodiment the Vickers hardness of the material of the bone screw is in the range of 110 to 500% of the Vickers hardness of the material of the bone plate.

In another embodiment the Vickers hardness of the bone screw material is in the range of 201 to 600 HV.

The invention and further developments of the invention are explained in detail in the following using the partially schematic views of several exemplary embodiments.

In the drawings:

FIG. 11 shows a longitudinal section of an insert of the device according to the invention;

FIG. 12 shows a top view of an insert of a device according to the invention;

FIG. 13 shows a view of a bone plate of a device according to the invention from below;

FIG. 14 shows an enlarged view of FIG. 13;

FIG. 15 shows a longitudinal section of FIG. 13;

FIG. 16 shows an enlarged view of FIG. 15;

FIG. 17 shows a longitudinal section of the bone plate according to FIG. 15 with inserted insert;

FIG. 18 shows an enlarged view of FIG. 17;

FIG. 19 shows an enlarged longitudinal section of fa device according to the invention with an inserted screw and a deformed insert.

Figure 1:
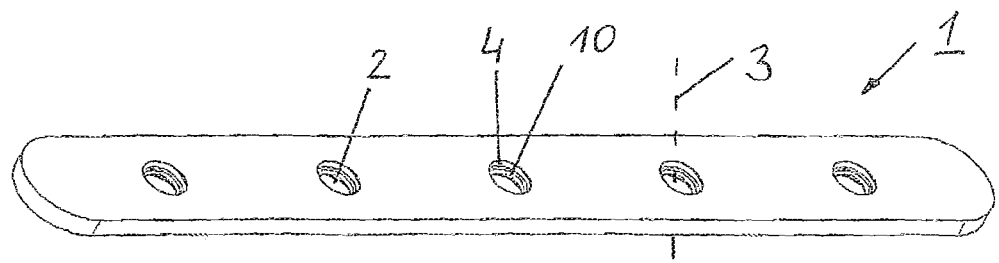
FIG. 1 shows a perspective view of an embodiment of the device according to the invention.

The embodiment shown in FIG. 1 of a device for bone fixation comprises a bone plate 1 with several plate holes 2 which each have a central axis 3 and an inner wall 4. The plate hole 2 is cylindrically constructed and is provided with an insert 10 which is suited for receiving a screw head. The outer wall of the insert 10 is congruent with the inner wall 4 of the cylindrical plate hole 2. The rotation-proof arrangement of the insert 10 in the plate hole 2 takes place by the positive locking after the deformation of the plate by the insert 10.

FIG. 1 shows a cylindrical insert 10 which is at first placed into the plate. The bone plate 1 is then deformed under force by a stamp so that the plate material flows over the insert 10. The securing against rotation and the axial security are given by the free positions of the insert 10.

The inserts 10 can also be conical.

Figure 2:
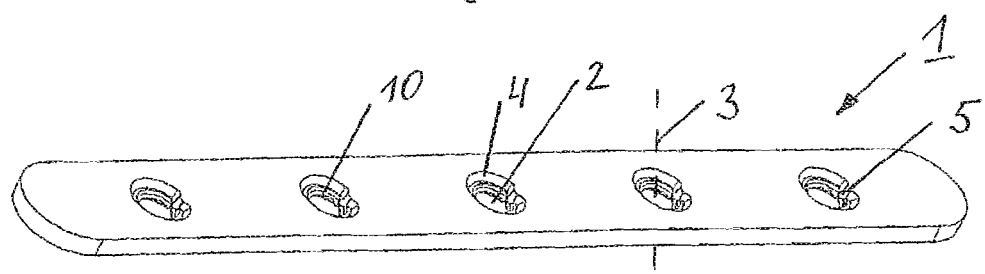
FIG. 2 shows a perspective view of another embodiment of the device according to the invention.

The embodiment shown in FIG. 2 comprises a bone plate 1 with several plate holes 2 which each have a central axis 3 and an inner wall 4. The plate hole 2 has an out of round or cylindrically interrupted shape and is provided with a projection 5 extending out of the inner wall 4 in the direction of the central axis 3. The plate hole 2 comprises an insert 10 suitable for receiving a screw head. The insert 10 comprises a slot 11 which fits the projection 5 (the 11 is not sketched in FIG. 2) so that the insert 10 is arranged in the plate hole 2 in a manner security against rotation.

Figure 3:
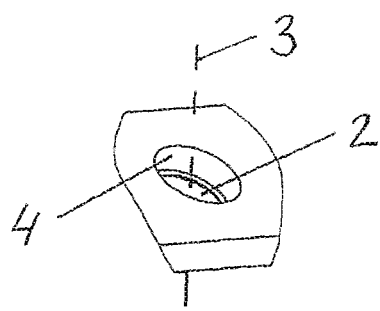
FIG. 3 shows a perspective view of an embodiment of the plate hole of the device according to the invention.

FIG. 3 shows a perspective view onto a part of a bone plate 1 with a plate hole 2 with a central axis 3 and an inner wall 4 without the inserted insert 10. The plate hole 2 is cylindrical.

Figure 4:
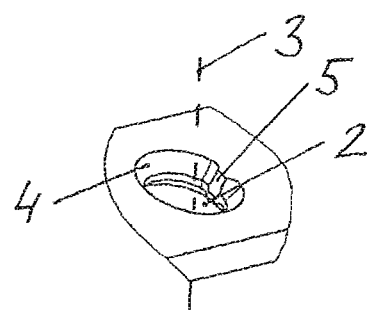
FIG. 4 shows a perspective view of another embodiment of the plate hole of the device according to the invention.

FIG. 4 shows a perspective view of a part of the bone plate 1 with a plate hole 2 with a central axis 3 and an inner wall 4 without the inserted insert 10. The plate hole 2 has an out of round or cylindrically interrupted shape. The inner wall 4 of the plate hole 2 is provided with a projection 5 extending in the direction of the central axis 3.

Figure 5:
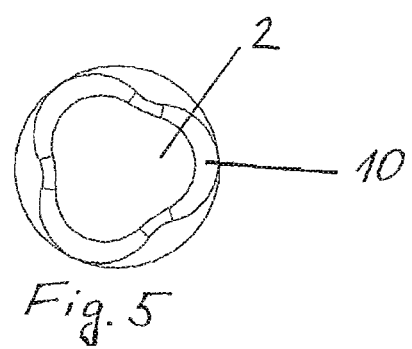
FIG. 5 shows a schematic view of another embodiment of the insert according to the invention for the device according to the invention.

FIG. 5 shows a schematic view of an insert 10 that has the shape of a polygon (triangle) with rounded corners.

Figure 6:
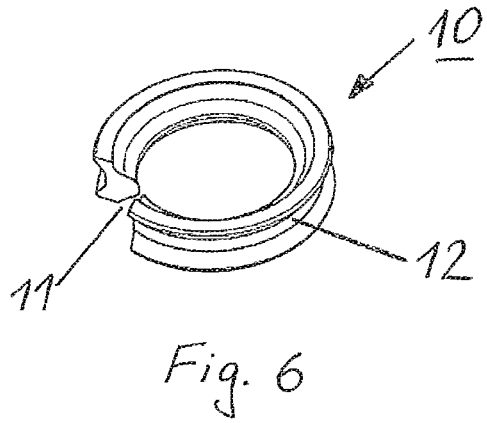
FIG. 6 shows a perspective view of an embodiment of the insert according to the invention.

FIG. 6 shows a perspective view of an insert 10 for a device for bone fixation. The insert 10 is provided with a continuous slot 11 with which the rotation-proof arrangement of the insert 10 in the plate hole 2 is achieved. The outer wall of the insert 10 has a radial groove 12 which makes possible a securing of the insert 10 in the plate hole 2 against axial shifting when the insert 10 is set into the plate hole 2 with corresponding everting material.

Figure 7:
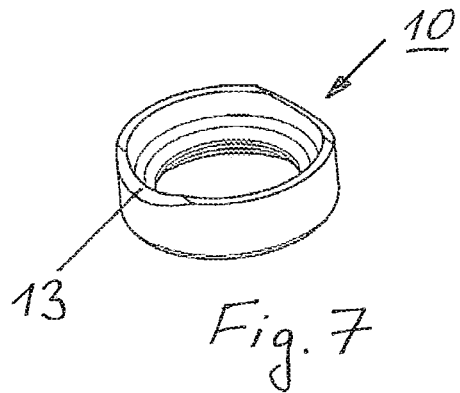
FIG. 7 shows a perspective view of another embodiment of the insert according to the invention.

FIG. 7 shows a perspective view of another insert 10 for a device for bone fixation. The insert 10 is provided with two notches 13 which—during the insertion of the insert 10 into the plate hole 2 with corresponding shoulders—are produced after the deformation (for example, by pressing, welding or stamping). The deformation and the corresponding production of the two notches brings about a securing against rotation and also a securing against axial shifting of the insert 10 in the plate hole 2.

Figure 8:
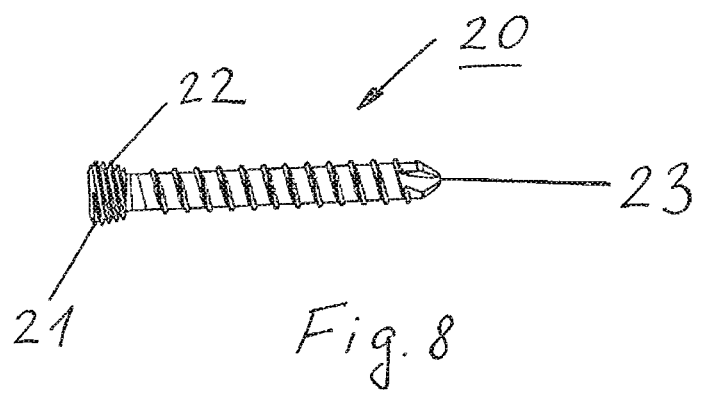
FIG. 8 shows a top view of an embodiment of the bone screw for the device according to the invention.

FIG. 8 is a top view of a bone screw 20 comprising a head 21 provided with an outer thread 22. The head 21 of the bone screw 20 tapers in the direction of the screw tip 23.

Figure 9:
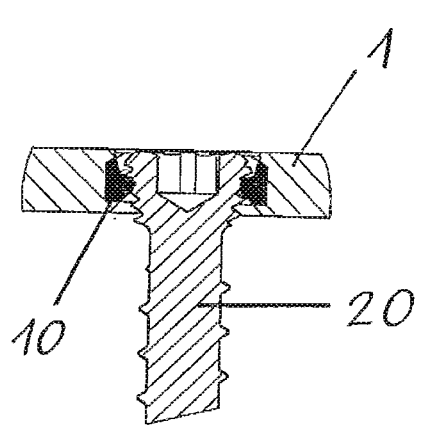
FIG. 9 shows a longitudinal section through an embodiment of a device according to the invention.

FIG. 9 shows a longitudinal section of a bone plate 1 with an inserted insert 10 and with a bone screw 20. The plate hole 2 has indentations in which the insert 10 is positioned so that the insert 10 is secured in the plate hole 2 against axial shifting. The locking of the screw head 21 in the plate hole 2 takes place by the deformation/shaping of the hard screw head thread into the softer material of the insert 10 (titanium) by the harder material (steel) of the outer thread 22 of the head 21 of the screw 20. The insert 10 is arranged in the plate hole 2 in a manner secured against rotation so that it cannot rotate during the deformation procedure.

Figure 10:
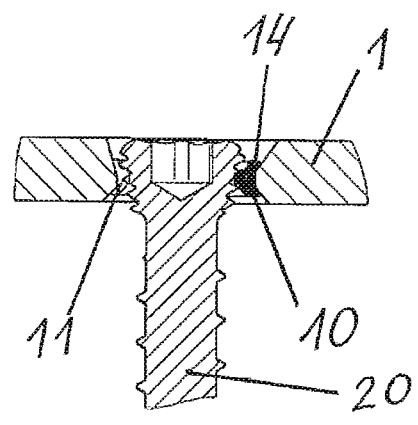
FIG. 10 shows a longitudinal section through another embodiment of a device according to the invention.

FIG. 10 shows a longitudinal section of another bone plate 1 with an inserted insert 10 and a bone screw 20. The insert 10 has a radial groove 12 (not shown in FIG. 10) which secures the insert 10 in the plate hole 2 against axial shifting by the corresponding eversion 14 of the plate hole 2. Furthermore, the insert 10 has a continuous slot 11. FIG. 10 shows the longitudinal section of an embodiment in which the longitudinal section runs through the slot 11. The locking of the screw head 21 (not shown in FIG. 10) in plate hole 2 takes place by the deformation of the softer material of the insert 10 (titanium) by the harder material of the outer thread 22 (not shown in FIG. 10) of the head 21 of the screw 20 (steel). The plate hole 10 has an out of round or cylindrically interrupted shape so that the insert 10 cannot rotate in the plate hole 2 during the screwing in procedure. The softer material (titanium) of the insert 10 is pressed into the harder material (steel) of the bone plate 1 simultaneously with the deformation of the material of the insert 10 by the screw 20. The resulting positive and non-positive locking secures the insert 10 rotationally and axially.

FIG. 11 shows a cylindrical insert 10 in a sectional view with a 2-fold conical inner geometry and a narrow, cylindrical rib. FIG. 12 shows a top view of the insert 10 with a shoulder. FIG. 13 shows a bone plate 1 with the plate holes 2 in a view from underneath. FIG. 14 is an enlargement of the latter. FIG. 15 shows a longitudinal section of the same bone plate 1 and FIG. 16 shows the enlargement of FIG. 14. FIG. 16 shows a plate hole 2 with a cylindrical profile with 2 shoulders. In FIG. 16 this is lower at the top than at the bottom. In addition, the plate hole 2 has four free positions which are placed only on one side; they will serve later for the securing of the rotation.

Procedure:

The insert 10 is pressed or laid into the bone plate 1 from the side which has no free positions. Subsequently, the lower part of the insert 10 is deformed with a stamp into the shoulder with the free positions, for example, with the press. Therefore, the material flows into the free position and the shoulders. The positive locking, the securing against rotation and the axial securing are given. This can be recognized in FIG. 17 and FIG. 18. FIG. 19 shows a formed-in bone screw with the deformed insert 10 and with the bone plate 1.

The following material combinations are especially suitable for the present invention. Grades 2 and 4 designated pure titanium with different degrees of purity. Titanium grade 2 is an unalloyed titanium with an average hardness of 150 HV (Vickers hardness). Titanium grade 4 is an unalloyed titanium with an elevated oxygen content and with an average hardness of 250 HV (Vickers hardness).

| Plate material | Insert material | Screw material |
| --- | --- | --- |
| Titanium grade 4 | Titanium grade 2 | Titanium grade 4 1.4441 implant steel |
| Cobalt-chrome-molybdenum CCM | Titanium grade 2 | Titanium grade 4 1.4441 implant steel |
| 1.4441 implant steel | Titanium grade 2 | Titanium grade 4 1.4441 implant steel |

The invention claimed is:

1. A device for bone fixation, comprising:
a bone plate provided with a plate hole; and
a hollow cylindrical or hollow conical insert supported in the plate hole,
said insert abutting at least partially an inner wall of the plate hole and being configured to receive a head of a bone screw;
wherein the entire bone plate, including the inner wall of the plate hole,
consists of a material with a Vickers hardness $H_P$,
wherein the insert consists of a material with a Vickers hardness $H_E$,
wherein $H_E < H_P$,
wherein the plate hole has an out of round shape,
wherein the insert is positively locked in the plate hole by:
(i) a cylindrically interrupted shape of the plate hole; or
(ii) an elliptical shape of the plate hole; or
(iii) a stop in the plate hole,
such that the insert cannot shift inside the plate hole, cannot pivot inside the plate hole and cannot rotate inside the plate hole, and
wherein the Vickers hardness $H_E$ of the material of the insert is in a range of 20% to 90% of the Vickers hardness $H_P$ of the material of the bone plate.

2. The device according to claim 1, wherein the Vickers hardness $H_E$ of the material of the insert is in the range of 120 to 200 HV.

3. The device according to claim 1, wherein the Vickers hardness of the material $H_P$ of the bone plate is in the range of 201 to 600 HV.

4. The device according to claim 1, wherein the bone plate and the insert each consist of a metal or a metal alloy.

5. The device according to claim 1, wherein the insert consists of pure titanium.

6. The device according to claim 1, wherein the plate hole has a central axis and wherein the insert is arranged concentrically to the central axis.

7. The device according to claim 1, wherein the insert has a through slot.

8. The device according to claim 1, wherein the insert has a cross section in a form of a circle with at least one non-circular portion.

9. The device according to claim 1, wherein the insert has a cross section in a form of a polygon.

10. The device according to claim 1, wherein an outside diameter of the insert is greater than an inside diameter of the plate hole.

11. The device according to claim 1, further comprising a bone screw which comprises a head with an outside thread.

12. The device according to claim 11, wherein the head of the bone screw tapers at least partially in a direction of a screw tip.

13. The device according to claim 11, wherein the head of the bone screw consists of a material with a hardness $H_S$, and wherein $H_S > H_E$.

* * * * *